(12) United States Patent
Cole et al.

(10) Patent No.: US 12,708,519 B1
(45) Date of Patent: Aug. 18, 2026

(54) DEVICES, SYSTEMS, AND METHODS FOR MANAGING COMPRESSION AND ALIGNMENT OF JOINTS

(71) Applicants: Mark Cole, Santa Ana, CA (US); Eduardo Chi Sing, Dana Point, CA (US)

(72) Inventors: Mark Cole, Santa Ana, CA (US); Eduardo Chi Sing, Dana Point, CA (US)

( * ) Notice: Subject to any disclaimer, the term of this patent is extended or adjusted under 35 U.S.C. 154(b) by 861 days.

(21) Appl. No.: 17/861,195

(22) Filed: Jul. 9, 2022

Related U.S. Application Data

(60) Provisional application No. 63/220,174, filed on Jul. 9, 2021.

(51) Int. Cl.
*A61F 2/44* (2006.01)
*A61F 2/38* (2006.01)

(52) U.S. Cl.
CPC ........... *A61F 2/442* (2013.01); *A61F 2/3859* (2013.01)

(58) Field of Classification Search
CPC .......... A61F 2/44; A61F 2/442; A61F 2/4425; A61F 2002/443
See application file for complete search history.

(56) References Cited

U.S. PATENT DOCUMENTS

| | | | | |
|---|---|---|---|---|
| 6,599,321 | B2 * | 7/2003 | Hyde, Jr. | A61F 2/40 623/18.12 |
| 10,507,111 | B2 * | 12/2019 | Johnson | A61F 2/30 |
| 2007/0179493 | A1 * | 8/2007 | Kim | A61F 2/442 606/33 |
| 2007/0233251 | A1 * | 10/2007 | Abdou | A61F 2/4425 623/17.11 |
| 2020/0022818 | A1 * | 1/2020 | Cook | A61F 2/4425 |

* cited by examiner

*Primary Examiner* — Larry E Waggle, Jr.
(74) *Attorney, Agent, or Firm* — William A. English; Vista IP Law Group LLP

(57) ABSTRACT

Devices, systems, and methods are provided that include correlated magnet structures ("programmable magnets") to manage compression, rotation forces, and/or alignment of bone joints in a human body. The joints may include the knee, spine, hip, and the like. In one example, correlated magnet assemblies are implanted directly into bones adjacent the joint. In another example, plates may be implanted between adjacent bones, e.g., adjacent vertebrae, that may be receive magnet assemblies.

20 Claims, 18 Drawing Sheets

3
10
5
8

3

10
5

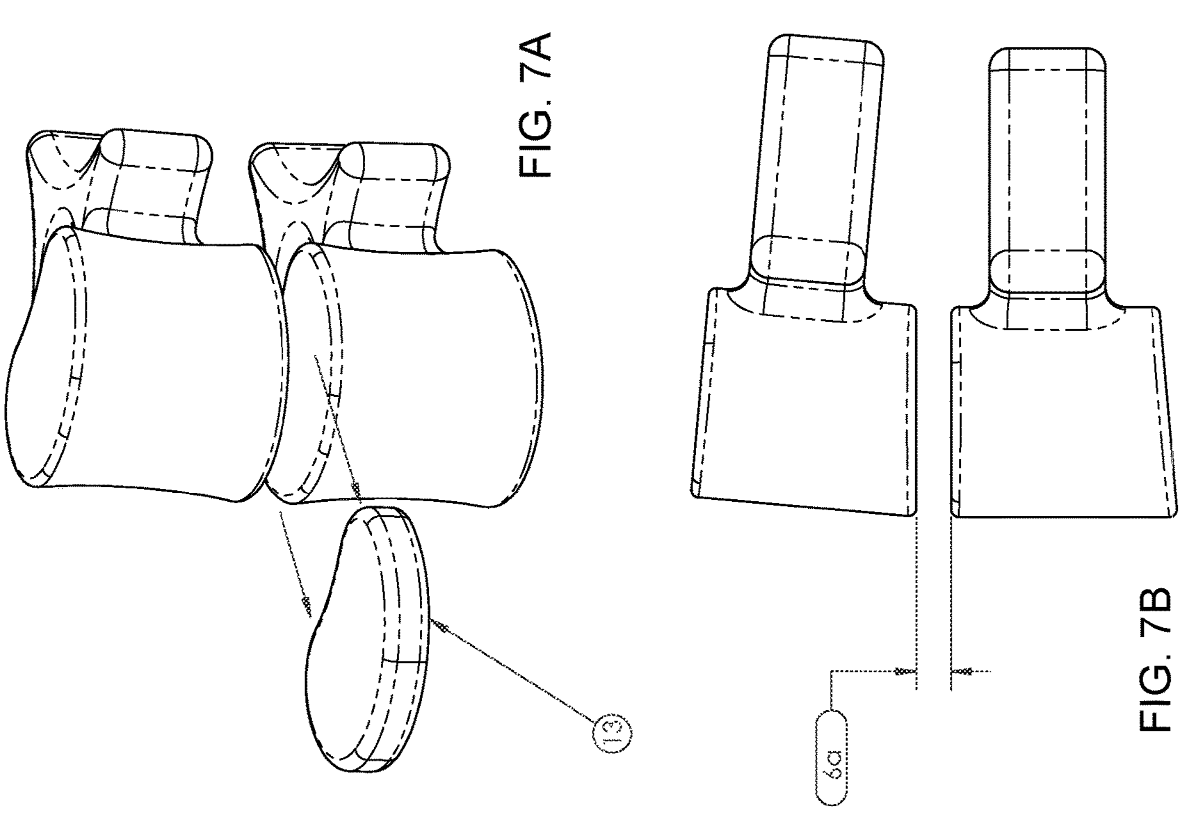
FIG. 7A
FIG. 7B
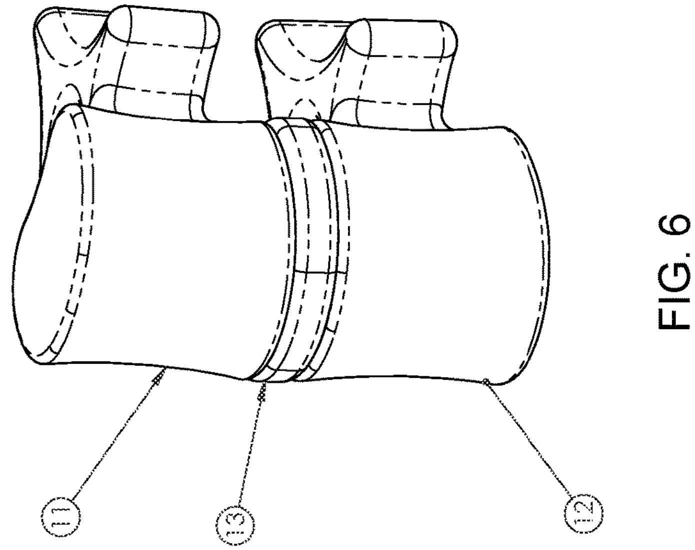
FIG. 6

17
15
15c
11
12
18

16
11
12
17
17c
17c
17b 22
19
22
20
22

14a

22

22
18
22
21
22

24
19

14a
19

23

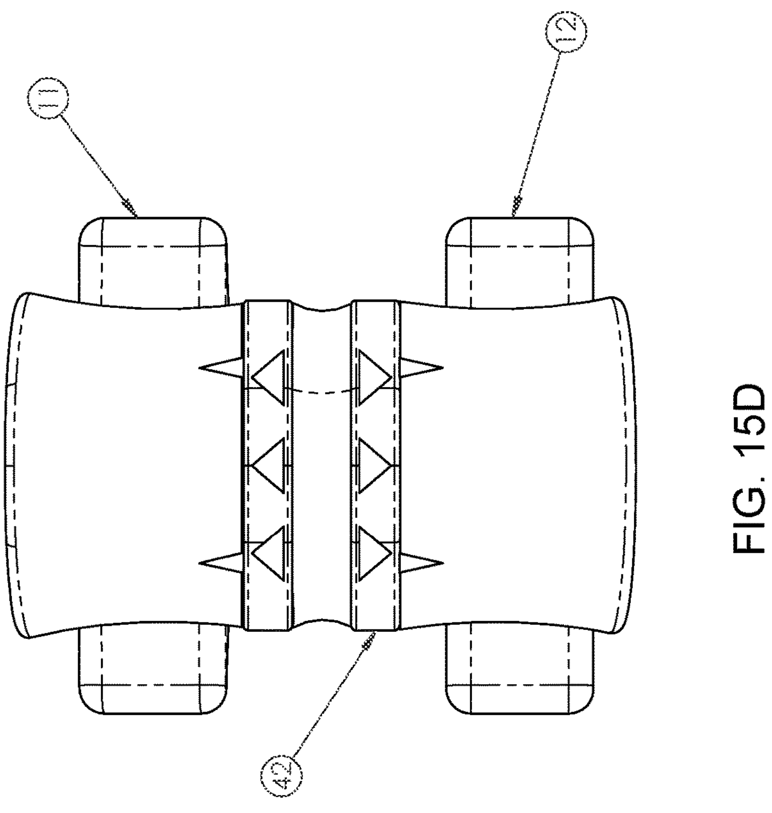
FIG. 15D
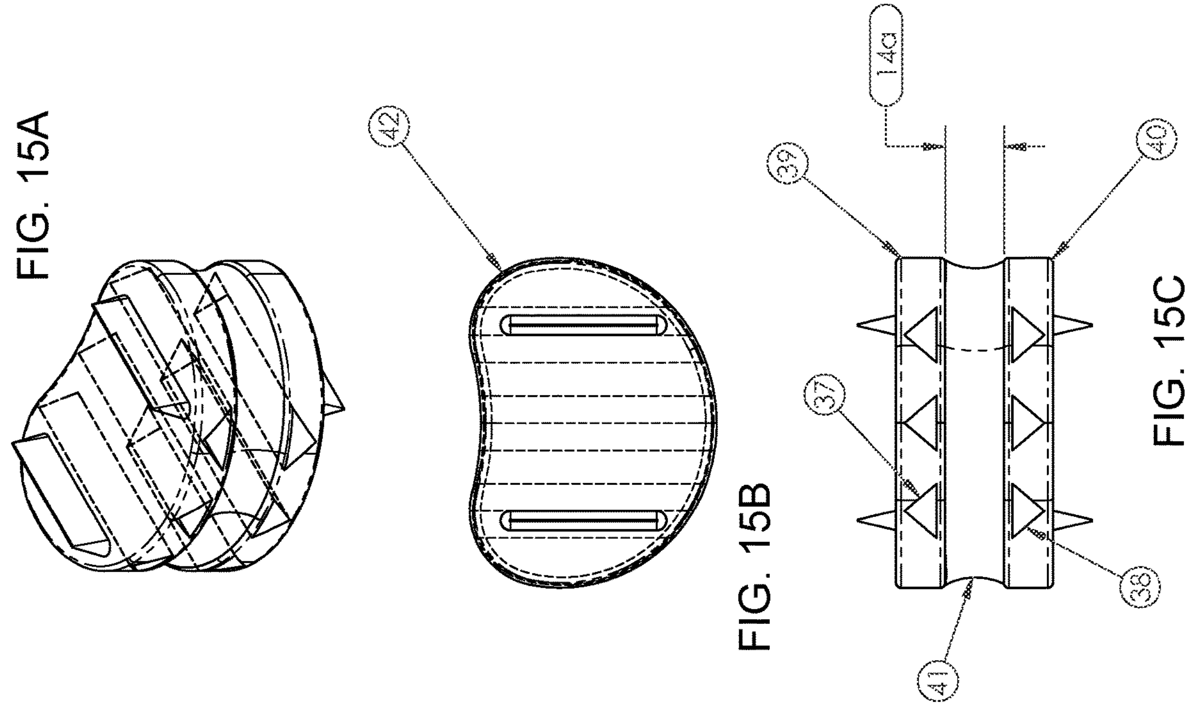
FIG. 15A
FIG. 15B
FIG. 15C 32
28
33

34
32
33
28
35

33

DEVICES, SYSTEMS, AND METHODS FOR MANAGING COMPRESSION AND ALIGNMENT OF JOINTS

RELATED APPLICATION DATA

The present application claims benefit of U.S. provisional application Ser. No. 63/220,174, filed Jul. 9, 2021, the entire disclosure of which is expressly incorporated by reference herein.

TECHNICAL FIELD

The present application is related to devices and methods related to orthopedic surgery and, more particularly, to devices and methods that use correlated magnet structures ("programmable magnets") to manage compression, rotation forces, and/or alignment of bone joints in a human body.

SUMMARY

The present application is directed to devices and methods related to orthopedic surgery and, more particularly, to devices and methods that use correlated magnet structures ("programmable magnets") to manage compression, rotation forces, and/or alignment of bone joints in a human body. The joints may include but are not limited to knee, spine, hip, and the like.

Correlated magnets may provide the ability to control or minimize compression and rotational forces, and/or to precisely align joint structures during articulation/motion of the joints via magnetic source coding and programming. Additional information regarding Correlated Magnetism, including correlated magnetic devices and methods for making and using them, may be found in U.S. Pat. Nos. 7,750,781, 7,755,462, 7,800,471, 7,817,004, and 7,868,721, and U.S. Publication No. 2009/0278642, the entire disclosures of which are expressly incorporated by reference herein. These references disclose exemplary processes to create and design magnets with a programmed magnetic field code capable of generating a custom correlated magnetic field between two or more corresponding magnets.

A correlated magnet, unlike conventional magnetic structures, offers varying parameters (e.g., size, shape number, magnetic field strength, and/or polarity) in each of the magnetic sources that make up the correlated magnetic structure, as disclosed in the references incorporated by reference above. By varying the code resolution of the magnetic sources (Maxels), the design of the magnet may have custom magnetic field characteristics. For example, the magnets may be customized to have specific attractive and repulsive forces at a specified gap between the two magnets. These magnets may control near and far field interactions to address and manage compression, rotational forces, and/or alignment elements present in the motion/articulation of a particular joint.

In accordance with one example, a system is provided for supporting a knee joint between a femur and a tibia that includes a first set of implants configured for implantation on or in a lower end of the femur; and a second set of implants configured for implantation on or in an upper end of the tibia, wherein each set of implants includes a plurality of magnet assemblies comprising correlated magnets configured to provide a desired spatial gap and alignment of the femur and tibia during motion of the knee joint In accordance with another example, a method is provided for supporting a knee joint between a femur and a tibia that includes implanting a first set of implants on or in a lower end of the femur; and implanting a second set of implants on or in an upper end of the tibia, wherein each set of implants includes a plurality of magnet assemblies comprising correlated magnets configured to provide a desired spatial gap and alignment of the femur and tibia during motion of the knee joint.

In accordance with still another example, a system is provided for supporting first and second adjacent vertebrae of a spine that includes a first plate configured for mounting to an upper surface of a first vertebral body; a second plate configured for mounting to a lower surface of a second vertebral body opposite the upper surface of the first vertebral body; and first and second correlated magnet assemblies configured to be secured to the first and second plates, respectively, to provide a desired spatial gap between the first and second vertebral bodies.

In accordance with yet another example, a method is provided for supporting a first and second vertebrae of a spine that includes mounting a first plate to an upper surface of a first vertebral body; mounting a second plate to a lower surface of a second vertebral body opposite the upper surface of the first vertebral body; securing a first correlated magnet assembly to the first plate; and securing a second correlated magnet assembly to the second plate such that the magnet assemblies are spaced apart from one another to provide a desired spatial gap between the first and second vertebral bodies.

In accordance with another example, a system is provided for supporting a hip joint between a pelvis and a femur that includes one or more first implants configured for implantation on or in an upper end of the femur; and one or more second implants configured for implantation around an acetabulum of the pelvis, wherein each of the implants includes a plurality of magnet assemblies comprising correlated magnets configured to provide a desired spatial gap and alignment of the femur relative to the pelvis during motion of the hip joint.

Other aspects and features of the present invention will become apparent from consideration of the following description taken in conjunction with the accompanying drawings.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 6 shows an example of an intervertebral disk between vertebral bodies of a spine.

FIGS. 7A-7B show the disk being removed from between the vertebral bodies in FIG. 6.

FIGS. 15A-15C show an example of an artificial intervertebral disk including correlated magnet assemblies.

FIG. 15D shows the artificial intervertebral disk of FIGS. 15A-15C implanted between intervertebral bodies of a spine.

Figures 1A, 1B, 1C:
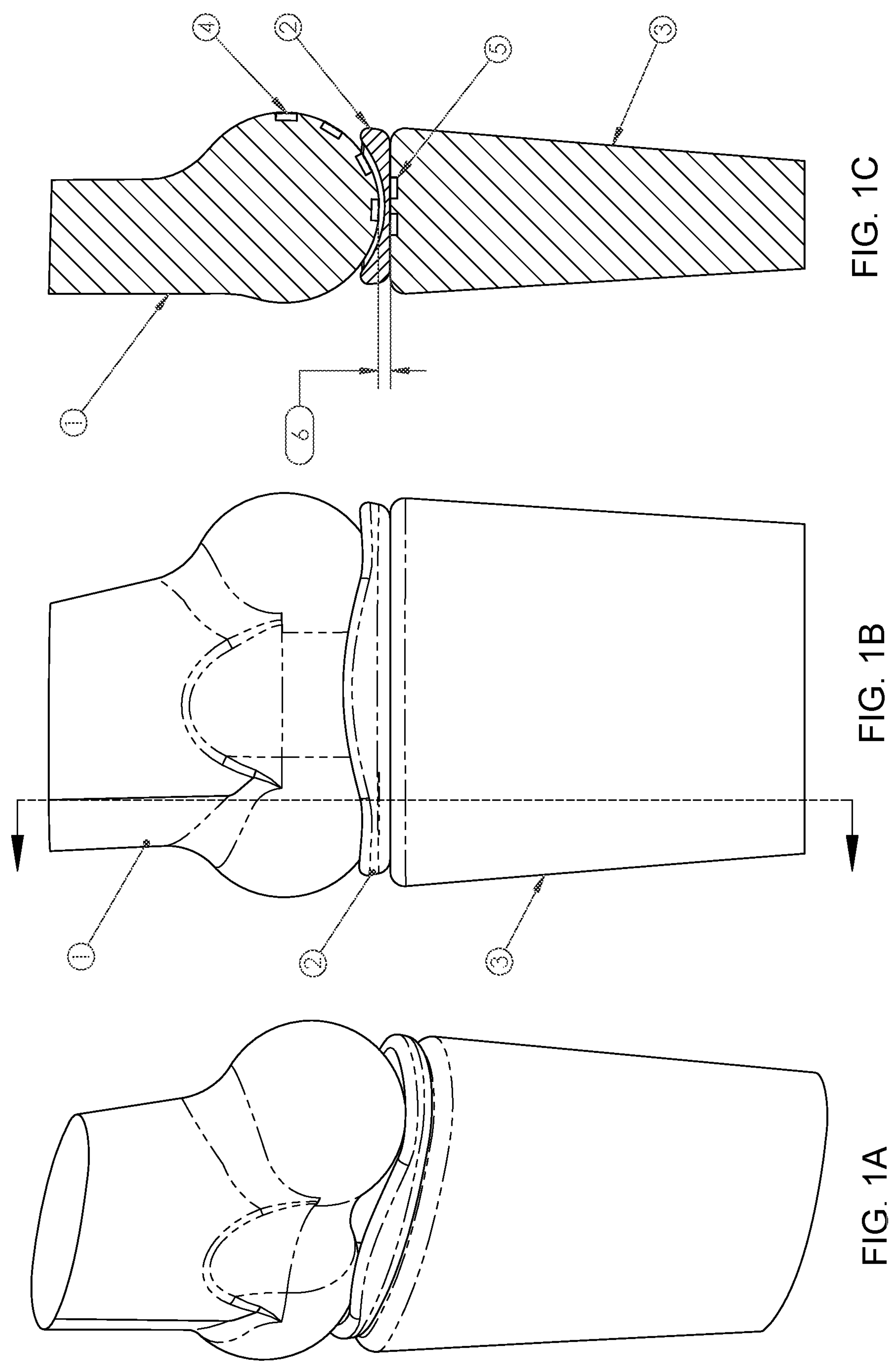
FIGS. 1A-1C show an example of a set of correlated magnet implants implanted in bones of a knee joint.

The drawings are not intended to be limiting in any way, and it is contemplated that various examples of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Before the examples are described, it is to be understood that the invention is not limited to particular examples described, as such may, of course, vary. It is also to be understood that the terminology used herein is for the purpose of describing particular examples only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Knee Joint Application

Turning to the drawings, FIG. 1A shows a knee joint structure including a femur 1, meniscus 2, and tibia 3 in an extended position. FIG. 1B is a front view of the knee joint. FIG. 1C is a cross sectional side view of the knee joint showing a set of correlated magnet structures implanted in bones adjacent the knee joint. As shown, embedded into the femur 1 distal end are a series of correlated magnet structures or implants 4. Similarly, the tibia 3 includes a corresponding set of magnet implants 5 embedded into the tibia 3, e.g., below articulate surface 2, thereby providing a spatial gap 6 between the two sets of corresponding correlated magnets 4, 5, as shown in FIG. 1C.

In the extended knee joint position, the embedded magnet implants 4, 5 may bias the joint to substantially maintain a predetermined spatial gap 6 between the two bone structures, e.g., to manage the compression forces exerted on the meniscus 2 by the weight of the body. The magnet implants 4, 5 may be designed with a specific correlated magnetic code to yield attractive and repulsive fields based on estimated compression forces and/or spatial gap requirements. The "shock absorption" mechanism created by the coded magnetic fields may allow for a natural degree of motion of the knee joint while minimizing compression forces when a gap is not present, and/or reducing compression forces when a gap is present. The mechanism may also provide the meniscus tissue with increased blood flow circulation and/or may provide relief of pain due to tissue and nerve compression. The magnets may be implanted and/or positioned at or below the exposed articulation surface of the bone structures, e.g., using standard minimal surgical techniques.

Figures 2A, 2B, 2C:
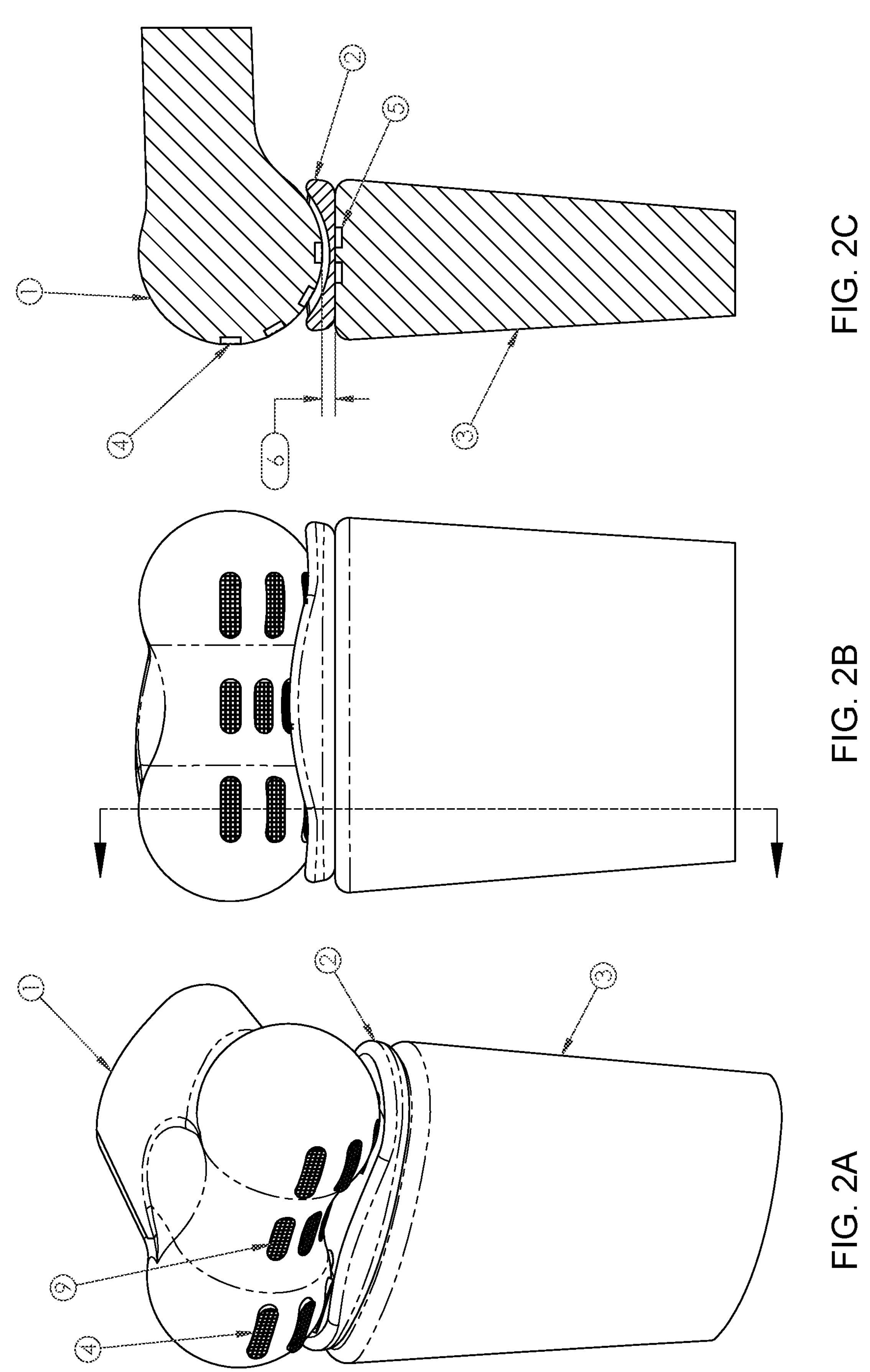
FIGS. 2A-2C show the knee joint of FIGS. 1A-1C with the knee bent.

FIGS. 2A-2C show the knee joint of FIGS. 1A-1C in a flexed position with an exemplary pair of sets of correlated magnet implants 4, 9 embedded in the femur 1. FIG. 2B is a front view showing an example of the correct alignment between the femur 1 and the tibia 3 in the flexed position. FIG. 2C shows a cross sectional side view of FIG. 2B with magnet implants 5, 4 in a rotated position relative to the position shown in FIGS. 1A-1C. FIG. 2C also shows that spatial gap 6 may be substantially maintained throughout the flexing motion of the knee joint.

Figures 3A, 3B:
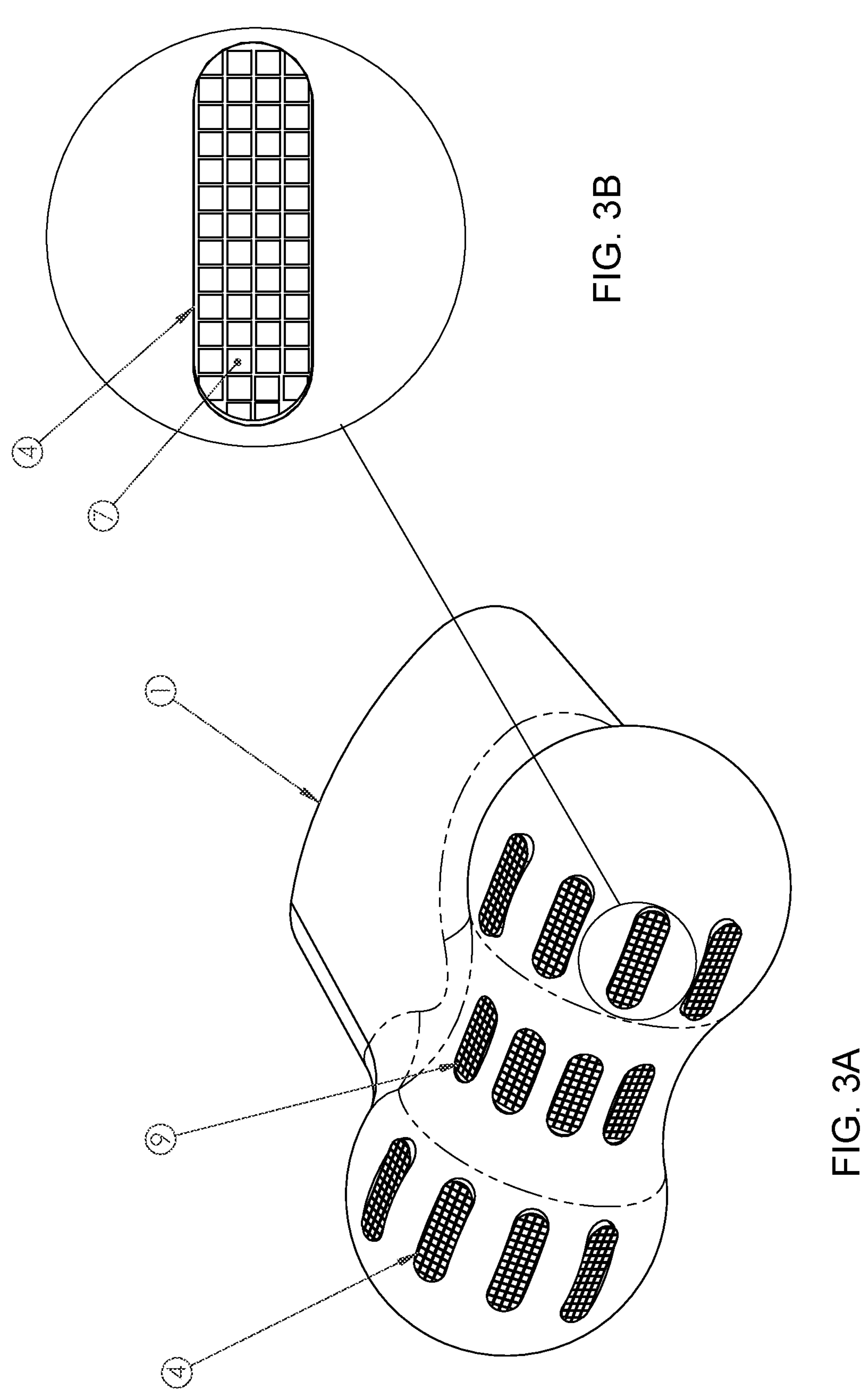
FIG. 3A is a detail of a lower end of a femur of the knee joint shown in FIGS. 1A-1C showing the correlated magnet implants.
FIG. 3B is a detail of an example of a correlated magnet implant.

FIG. 3A shows an exemplary set of magnet implants, including a plurality of rows of magnets 4, 9 embedded onto the surface of the femur 1, e.g., to provide desired spatial gap and/or alignment of the joint during movement of the joint. For example, the outer rows of magnets 4, e.g., implanted along the medial and lateral condyles of the femur, may be configured to substantially maintain the spatial gap 6 during the flexing motion/rotation of the knee. The center row of magnets 9, e.g., implanted along the intercondylar fossa, may be configured to substantially maintain correct alignment of the two bones. The magnets 9 may also be the main source for a repulsive magnetic field to manage most of the compression forces with the corresponding set of magnets embedded in the tibia 3. FIG. 3B is a detail showing an example of one of the magnets 4 with one of numerous potential coded densities and different Maxel configurations. The programmed magnetic code in the magnets 4 may be different than the magnets 9, e.g., due to the different actuation requirements in terms of alignment, rotation, compression forces, and/or spatial gap parameters.

Figures 4A, 4B, 4C:
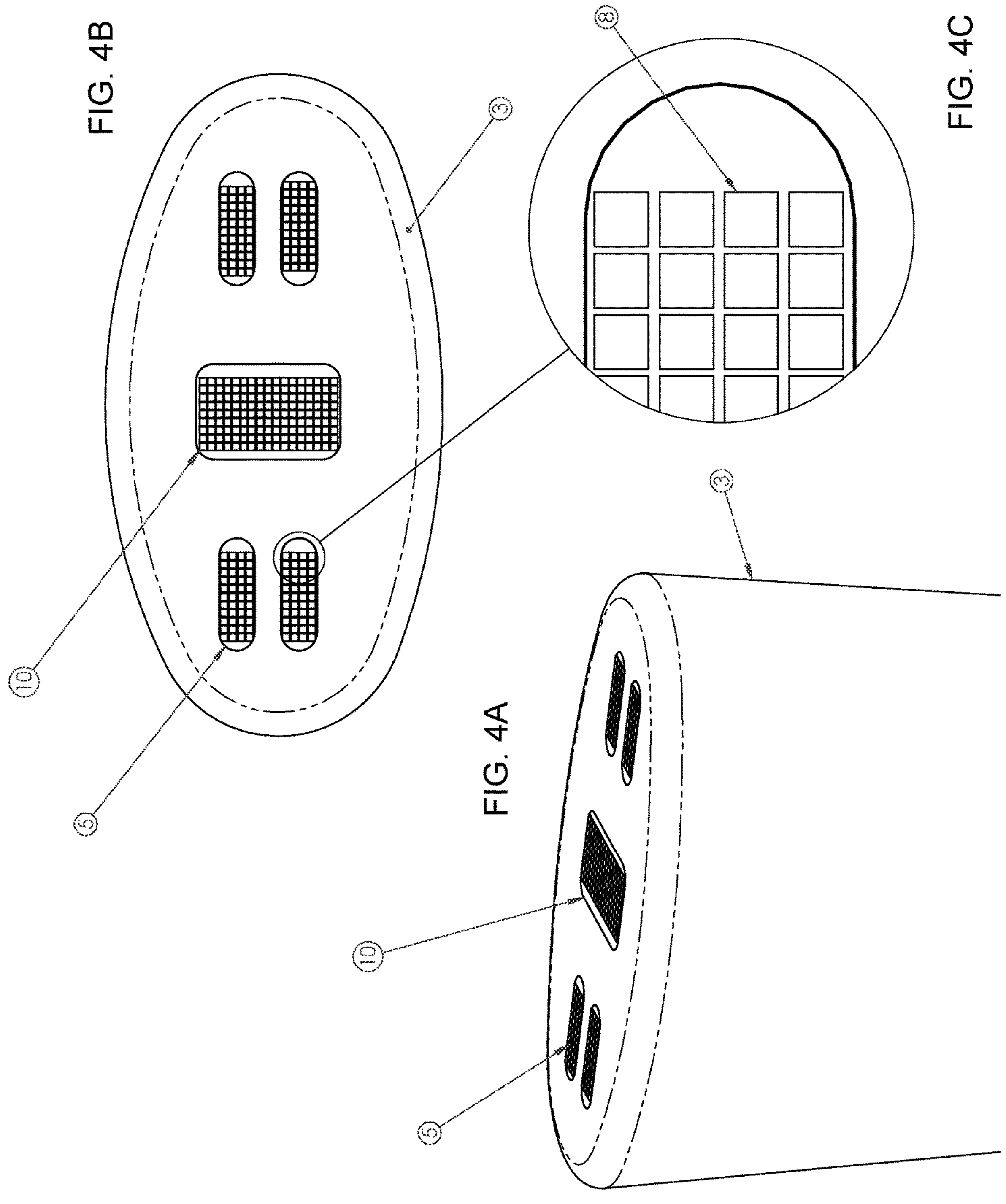
FIGS. 4A and 4B are perspective and top views, respectively, of an upper end of a tibia of the knee joint of FIGS. 1A-1C showing the correlated magnet implants.
FIG. 4C is a detail of an example of a correlated magnet implant.

FIGS. 4A and 4B show an exemplary corresponding set of correlated magnet implants embedded on the surface of the tibia 3. Magnets 5 may be coupled and/or interact with the magnets 4 in the femur 1, while magnet 10 may be coupled and/or interact with the magnets 9 (shown in FIG. 3A). The orientations of the magnet implants 5, 10 may be such that they maximize the ability for all magnets to align and/or manage compression forces in a flexed or extended joint position. FIG. 4C shows an exemplary programmed magnetic code that may be provided on the magnet implant 5. The numbers of magnets, size, and/or location may be readily determined by the articulation/motion requirements of the knee joint relative to estimated compression forces, spatial gap flexing angles, alignment, and/or other parameters. Another possible benefit of using correlated magnets, with specifically programmed magnetic field codes, is the ability to address joint articulation without moving components as part of the magnet system. There are no fatigue, creep, or usable life issues inherent in the magnetic components.

Figure 5A:
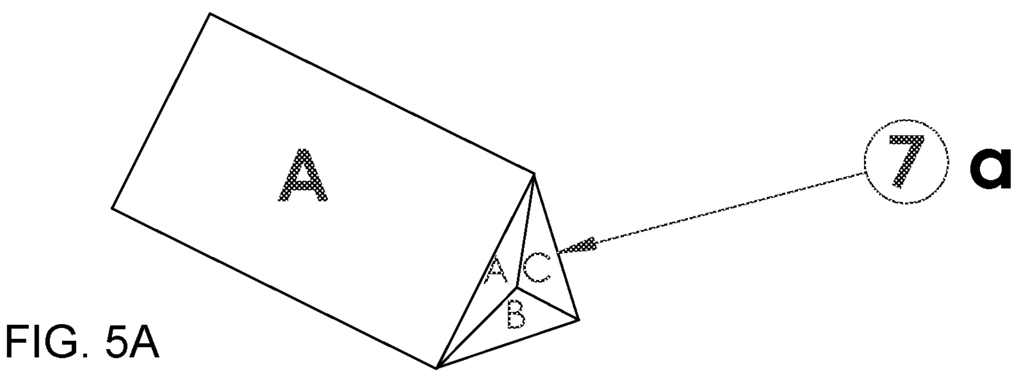
FIGS. 5A-5C show examples of correlated magnets having different shapes that may be included in a correlated magnet implant.
Figure 5B:
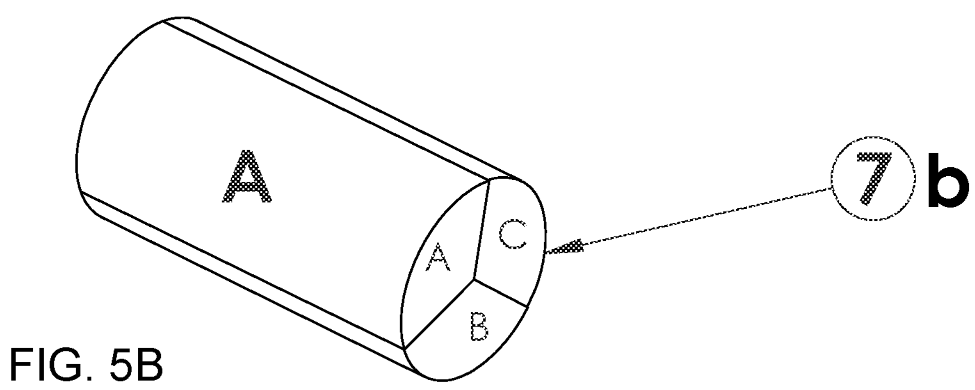
Figure 5C:
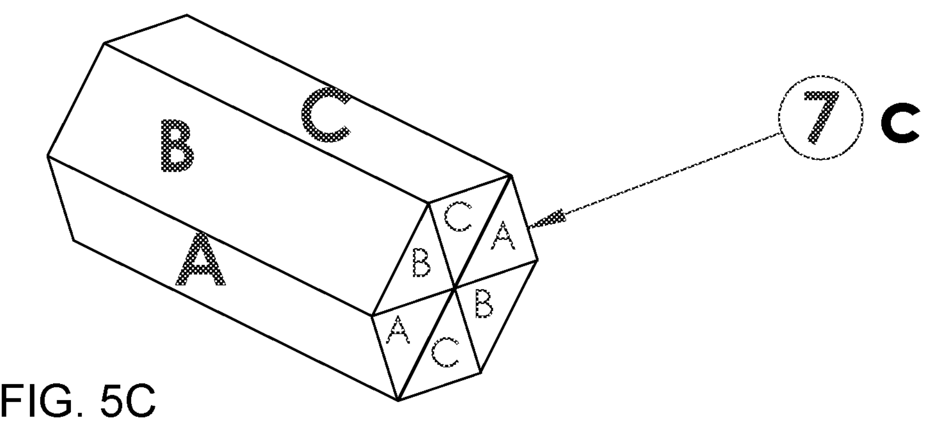

Turning to FIGS. 5A-5C, exemplary correlated magnets are shown having different shapes that may be included in a correlated magnet implant. For example, magnet array 7*a* shown in FIG. 5A includes a set of correlated magnets having a triangular shape where each of the planes may be programmed with different magnetic codes with several densities. Alternatively, magnet arrays 7*b* and 7*c* shown in FIGS. 5B and 5C may be included in the implants that offer additional degrees of freedom to the behavior of the magnetic fields. The combinations of magnet shapes along with magnetic codes are endless. The magnets may be temperately or permanently implanted at the joint structures.

The management of the articulation forces with correlated magnets may provide relief of pain and/or bone wear in the meniscus area, as well as the promotion of tissue growth. One of the features of using correlated magnets is the ability to program repulsive and attractive fields at a predetermined spatial gap/dimension. For example, as shown in FIGS. 1C and 2C, the spatial gap 6 may include a combination of filled space, e.g., by the meniscus, and non-filled empty space gap (not shown). The spatial gap configuration depends on the compression forces applied at the joint relative to the customized magnetic field interaction between the corresponding magnets.

Spine Application

Turning to FIG. 6, two vertebral bodies 11, 12 of adjacent vertebrae (e.g., L2 and L3) of a spine are shown along with an intervertebral disk 13. The following is another example where the use of correlated magnets may generate a suitable magnetic field interaction to substantially maintain a predetermined spatial gap between bone structures in an articulation/compression scenario. For example, as shown in FIGS. 7A and 7B, the intervertebral disk 13 may be removed, creating spatial gap 6*a* between vertebral bodies 11, 12, e.g., as shown in FIG. 7B. A system of implants including correlated magnets may then be implanted between the vertebral bodies 11, 12, e.g., to provide a desired spatial gap and/or alignment of the vertebral bodies 11, 12.

For example, FIGS. 8A-8D show an exemplary system 14 that includes a pair of plates 15, 17 that may be at partially implanted into and/or otherwise permanently attached to the vertebral bodies 11, 12, and correlated magnet assemblies 18, 19 that may be secured to respective plates 15, 17. Each plate 15, 17 may include a contact surface 15*a*, 17*a* configured for placement against a respective surface of the vertebral body 11, 12, e.g., including one or more features to enhance securing the plate 15, 17 to the respective vertebral body 11, 12. For example, as shown, each plate 15, 17 may include a pair of elongate ridges 15*b*, 17*b* that are spaced apart from one another on the contact surface 15*a*, 17*a*, e.g., extending substantially parallel to one another, that may be received in slots or grooves 16 formed in the vertebral bodies 11, 12, e.g., as described further below. The plates 15, 17 may have a generally circular or "D" shape around their outer periphery similar to the vertebral bodies 11, 12, e.g., such that the plates 15, 17 are generally coextensive with and/or do not extend radially outward from the vertebral bodies 11, 12 once implanted.

Figures 8A, 8B, 8C, 8D:
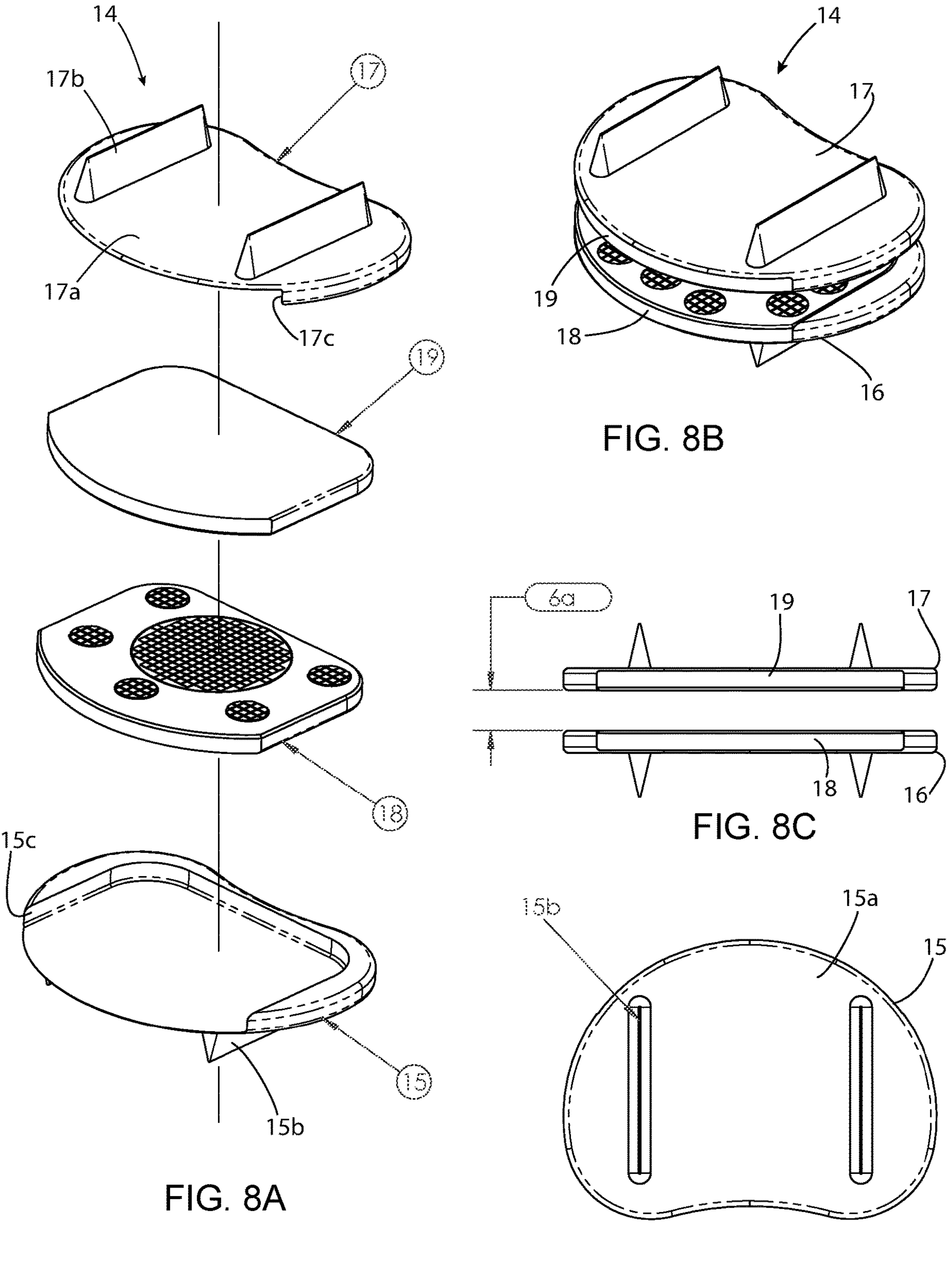
FIGS. 8A-8D are various views showing a system including plates and correlated magnet assemblies.

In addition, each plate 15, 17 includes a cavity or socket 15*c*, 17*c*, e.g., on an opposite side from the contact surface 15*a*, 17*a* configured to receive a correlated magnet assembly 18, 19. For example, as best seen in FIG. 8A, the socket 15*c*, 17*c* may include a sidewall extending partially around an outer periphery of the plate 15, 17, e.g., open on only one edge, such that a correlated magnet assembly 18, 19 may be inserted along the surface of the plate 15, 17 into the socket 15*c*, 17*c*. In the example shown, each assembly 18, 19 includes a substantially flat body having an outer shape similar to the plates 15, 17 and including an array of correlated magnets on at least one surface thereof, as described further below.

Optionally, the plates 15, 17 and/or correlated magnet assemblies 18, 19 may include one or more connectors (not shown) for securing the assemblies 18, 19 in the sockets 15*c*, 17*c*, e.g., to prevent the assemblies 18, 19 from sliding out once implanted. For example, one or more detents and corresponding pockets (not shown) may be provided that engage one another when the assembly 18, 19 is fully received in the socket 15*c*, 17*c*. In addition or alternatively, the assemblies 18, 19 may be secured by other methods, e.g., bonding with adhesive, fusing, crimping or bending (e.g., along the open edge), and the like, to prevent removal or displacement.

Figures 9A, 9B:
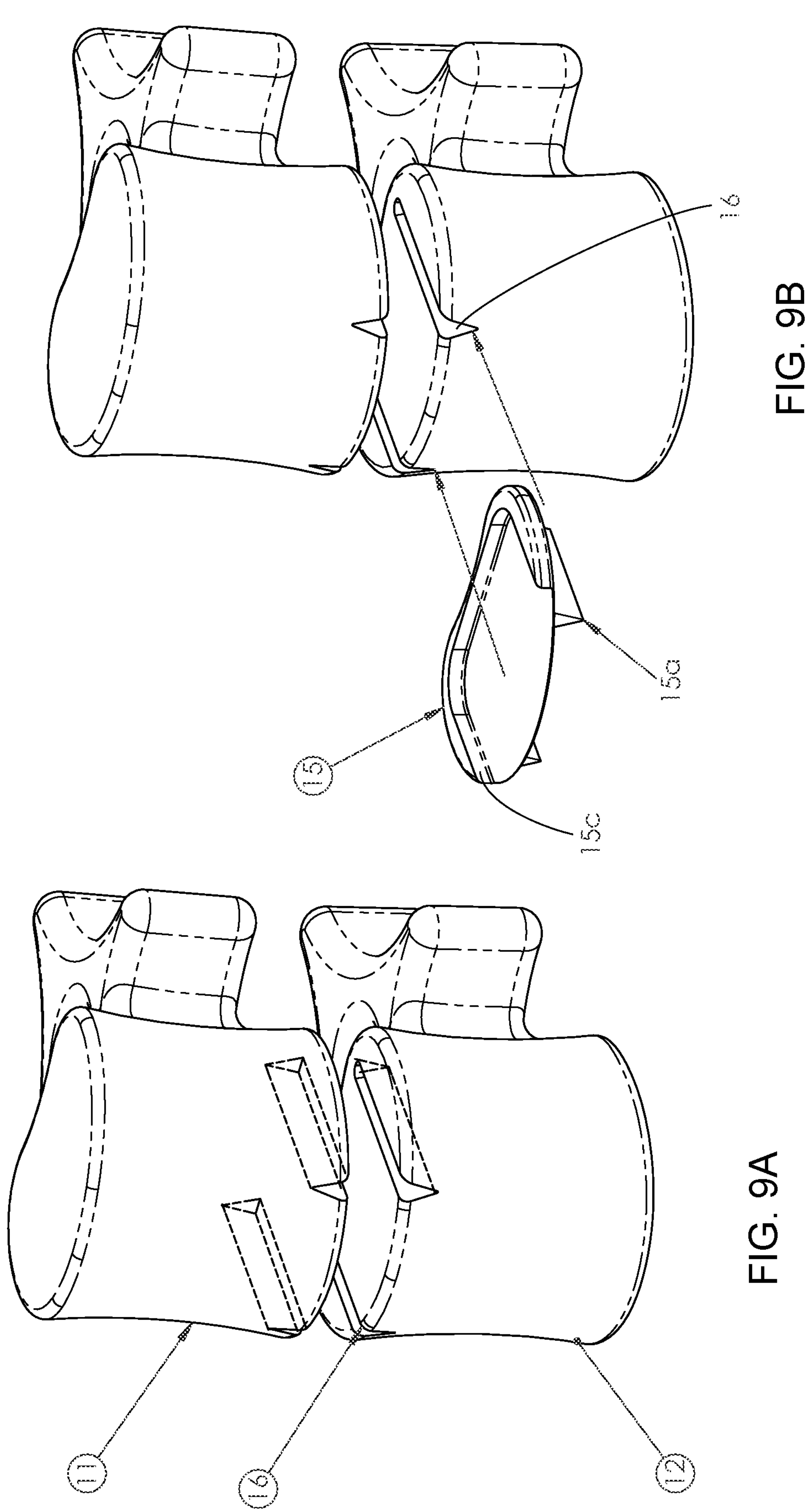
FIGS. 9A-9E show an exemplary method for implanting the plates of the system shown in FIGS. 8A-8D between the vertebral bodies of FIG. 6 to replace the disk.

Turning to FIGS. 9A-9E, an exemplary method is show for implanting the system 14 between two vertebral bodies 11, 12, e.g., after removal of the intervertebral disk 113, as shown in FIGS. 7A and 7B. Initially, as shown in FIG. 9A, a pair of grooves or slots 16 may be surgically created in the opposite surfaces of the vertebral bodies 11, 12, e.g., in the top surface of the L3 vertebral body 12, and in the bottom surface of the L2 vertebral body 11. The grooves 16 may create a location for subsequent placement of the plates 15, 17 using the ridges or other features 15*b*, 17*b* having complementary shapes to the grooves 16. For example, after exposure of the vertebral bodies 11, 12 and removal of the disk 13, a saw or other tool (not shown) may be used to create the grooves 16 from one edge of the cortical rim at least partially across the vertebral body 11, 12 towards the opposite edge.

Figures 9C, 9D:
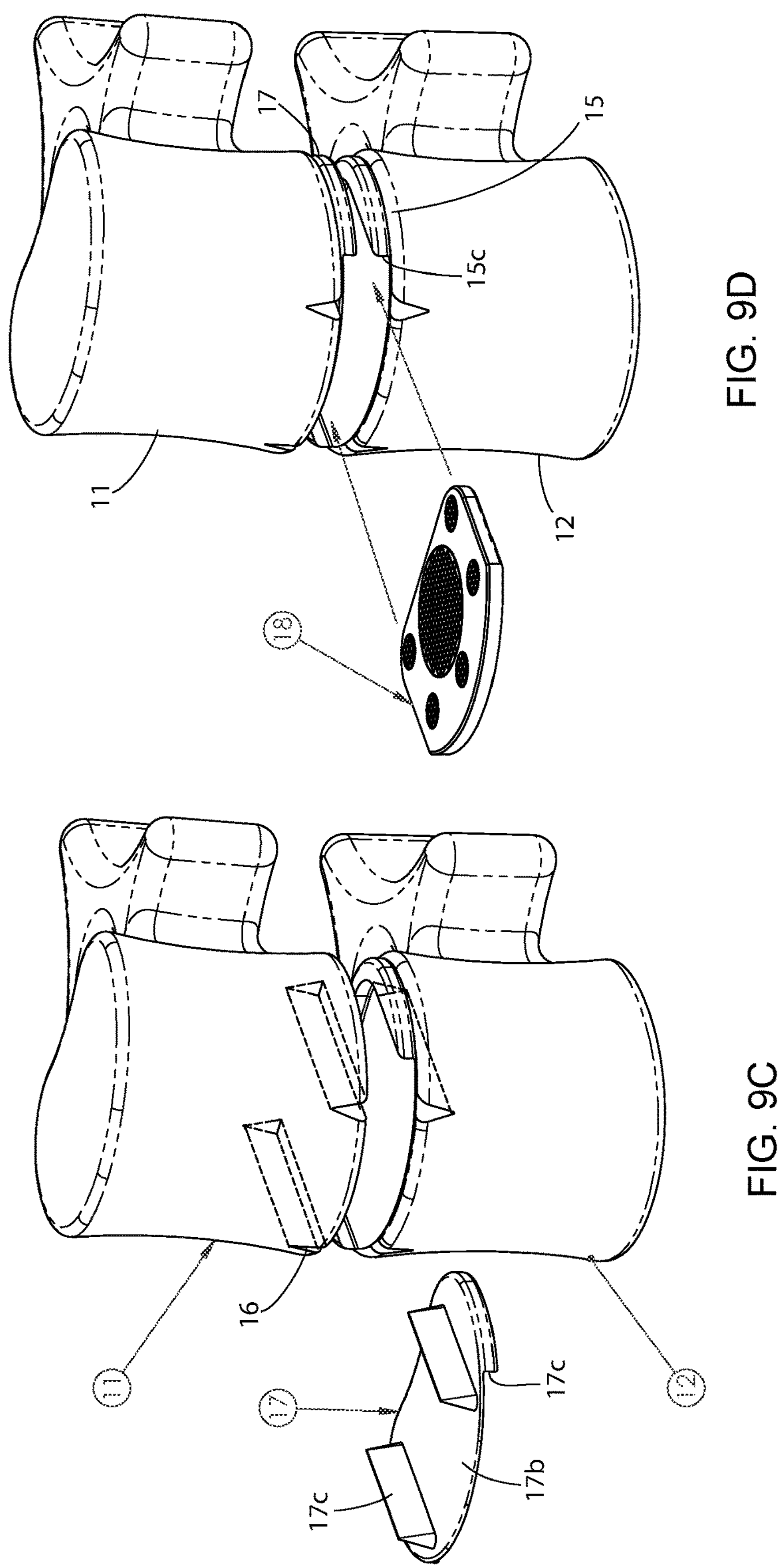

Turning to FIGS. 9B and 9C, the plates 15, 17 may be inserted into the space between the vertebral bodies 11, 12, e.g., by sliding the ridges 15*b*, 17*b* of each plate 15, 17 into the grooves 16 in the corresponding vertebral body 11, 12. Optionally, the ridges 15*b*, 17*b* may include one or more features, e.g., serrations, protrusions, textures, and the like (not shown) that may engage with the adjacent bone, e.g., to provide an interference fit and/or otherwise permanently or removably secure the plates 15, 17 in position. Optionally, the plates 15, 17 may be permanently attached to the vertebral bodies 11, 12, e.g., using bone cement or other adhesives.

Figures 9E, 10A, 10B:
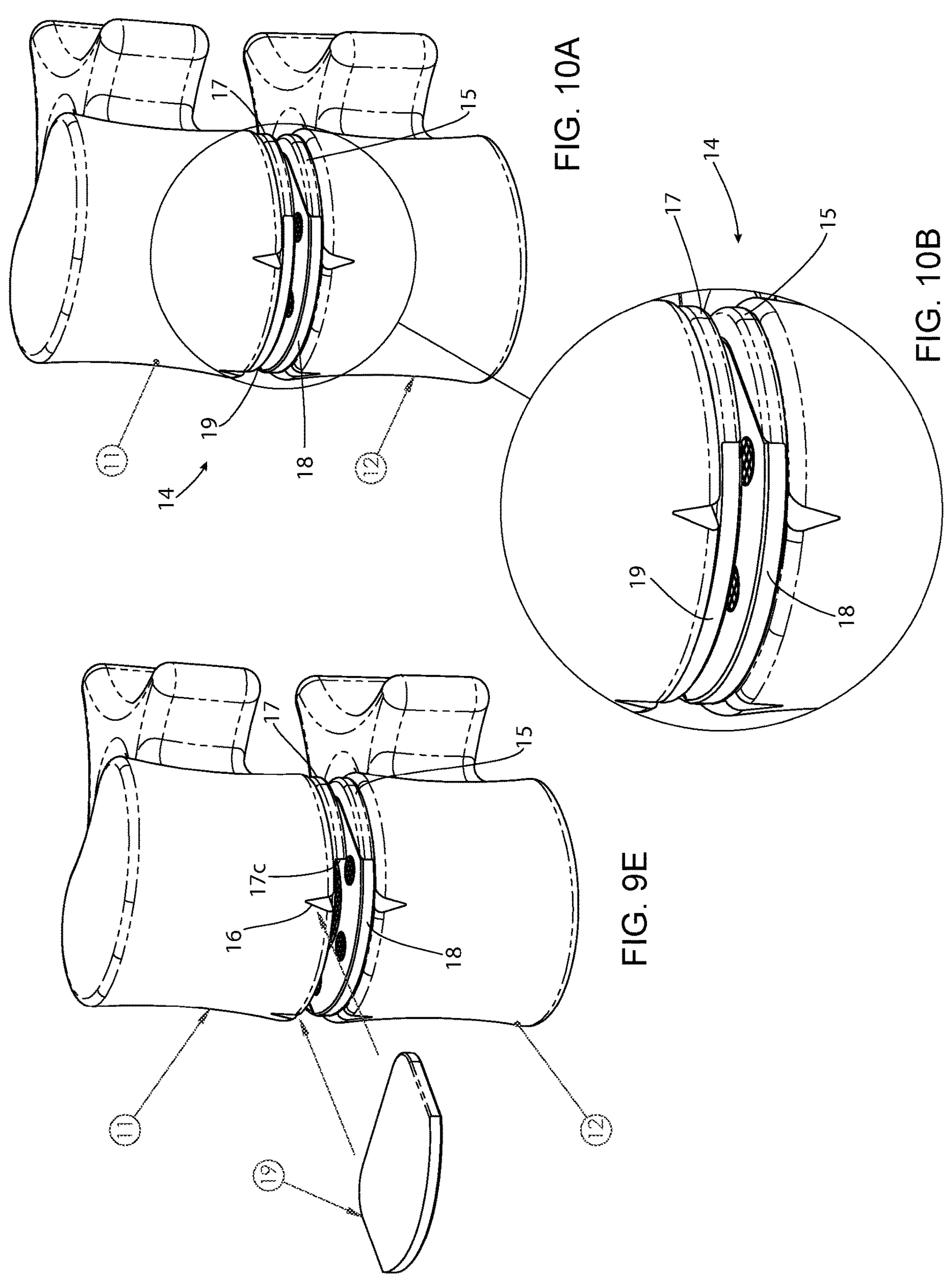
FIGS. 10A and 10B show the system of FIGS. 9A-9E after implantation between the vertebral bodies.
Figure 11B:
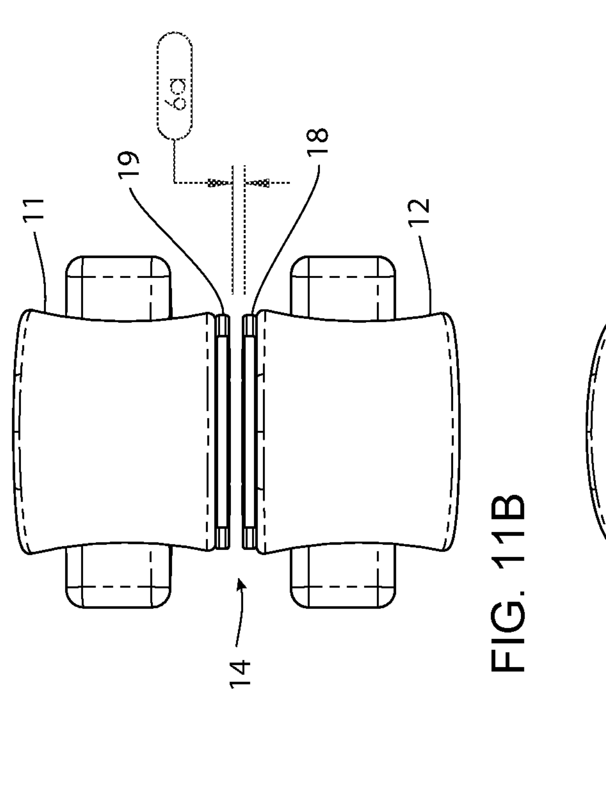
FIGS. 11A-11D show an exemplary system of correlated magnet assemblies implanted between vertebral bodies to achieve a desire spatial gap.
Figure 11D:
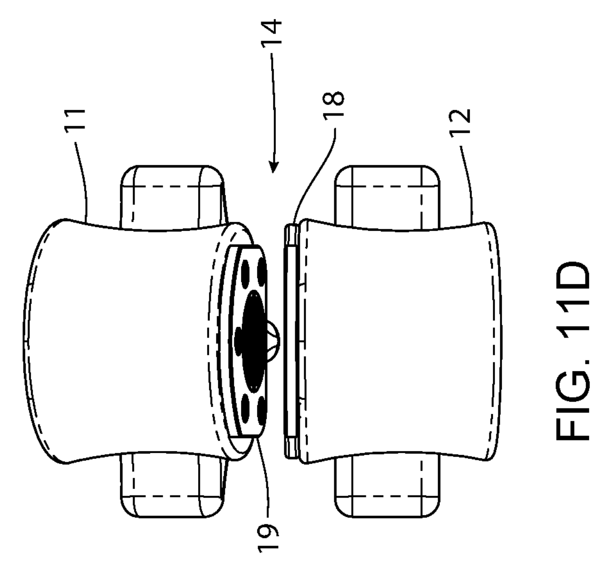
Figure 11A:
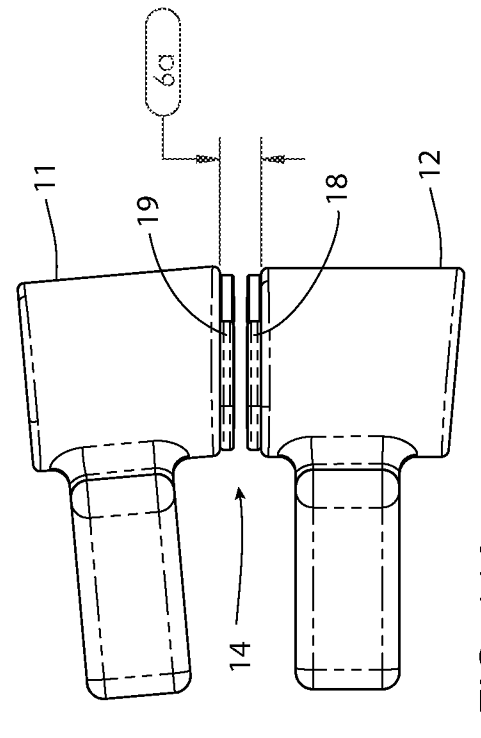
Figure 11C:
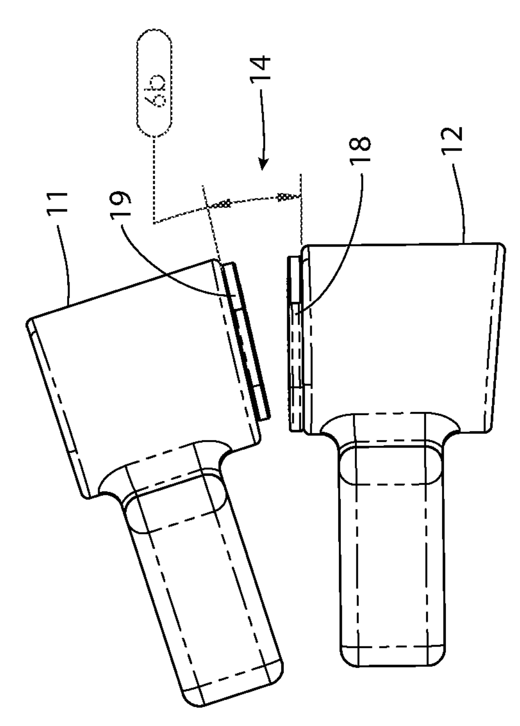

Turning to FIGS. 9D and 9E, with the plates 15, 17 fully seated, a correlated magnet assembly 18, 19 may then be inserted into each of the plates 15, 17. For example, the socket 15*c*, 17*c* of each plate 15, 17 may include a sidewall or other feature defining a cavity or socket that is open on one side such that the magnet assembly 18, 19 may be slid between the plates 15, 17 into the corresponding socket 15*c*, 17*c*. Each socket 15*c*, 17*c* may include a rim or one or more other guides, e.g. around one or more edges of the sidewall (not shown), to prevent the assembly 18, 19 from moving away from the respective plate 15, 17. Optionally, each assembly 18, 19 may be removably or substantially permanently secured to the respective plate 15, 17, e.g., before or after mounting the plates 15, 17 to the vertebral bodies 11, 12.

Turning to FIGS. 10A and 10B, the complete correlated magnetic system 14 is shown in place occupying the space left by the removal of disk 13. With the assemblies 18, 19 fully received in the respective plates 15, 17, a gap may remain between the assemblies 18, 19, e.g., as described further below.

Turning to FIGS. 11A-11D, an exemplary system 14 is shown implanted between vertebral bodies, 11, 12, e.g., of the L2 and L3 vertebrae. FIG. 10B is a front view of the system and 10 showing the vertebral bodies 11, 12 aligned correctly and spaced apart by spatial gap 6*a*. FIGS. 10C and 10D show the system 14 substantially managing and maintaining a different configuration of spatial gap 6*b*, e.g., as the subject moves during normal activity.

The coded correlated magnets embedded on assemblies 18, 19 may be programmed to generate magnetic field interaction suitable to maintain spatial gaps 6*a* and 6*b*, e.g., when compression and lateral forces are applied by the vertebral bodies 11, 12. Similar to other examples herein, the system 14 has no moving parts and may provide a natural articulated motion between the vertebral bodies 11, 12 with the motion degrees of freedom required by the spine. In addition, the modular nature of the system 14 may allow customized assemblies 18, 19 to be created for each individual subject, e.g., based on their physical condition, e.g., weight, level of activity, and the like, and then the customized assemblies 18, 19 may be implanted. Optionally, if desired, during a subsequent surgical procedure, the assemblies 18, 19 may be removed and a replacement set of assemblies 18, 19, e.g., including a different configuration of correlated magnets may be received in the plates 15, 17.

Figures 12A, 12B, 12C, 12D, 12E:
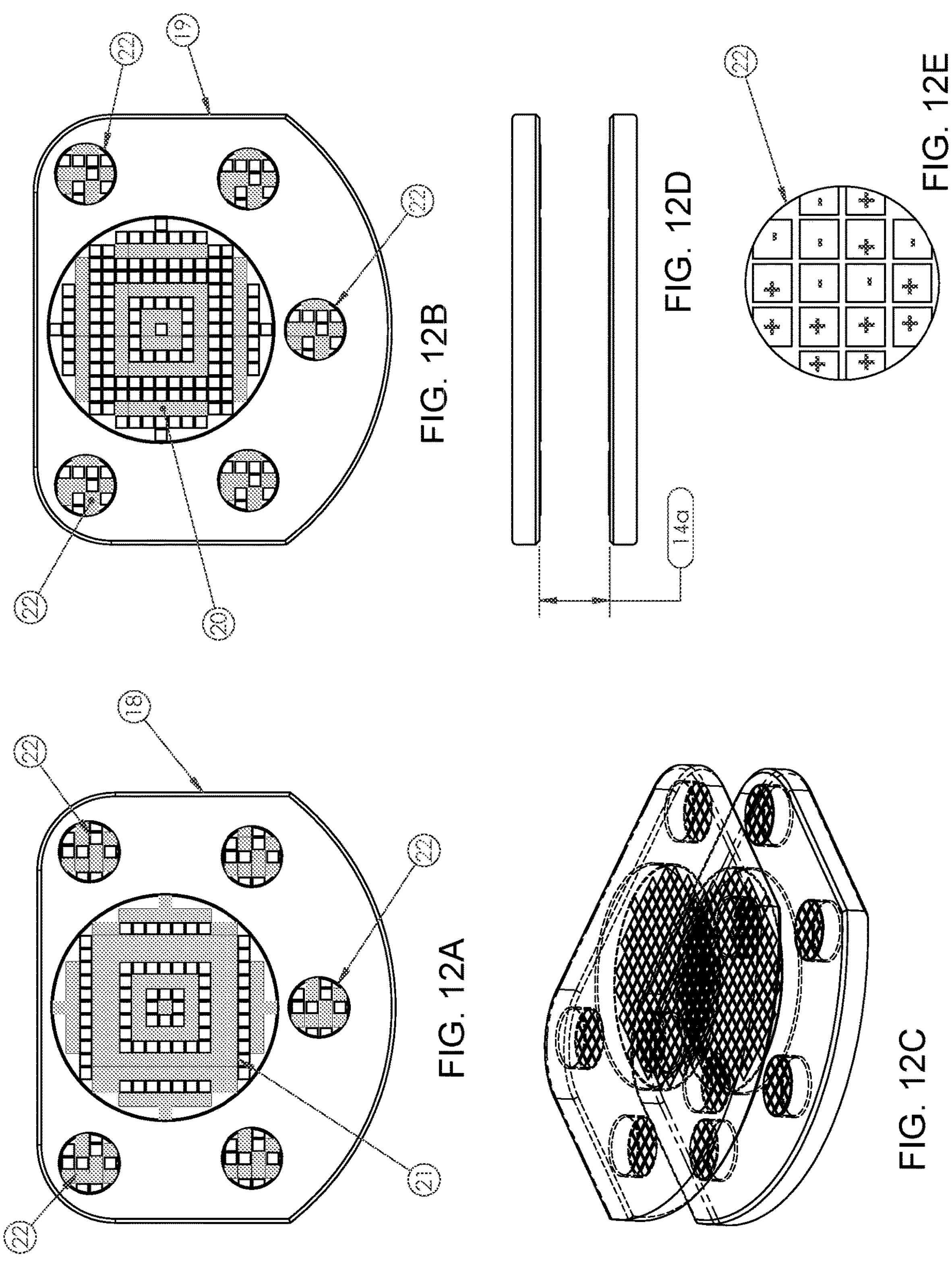
FIGS. 12A-12C show an example of correlated magnet assemblies that may be included in the system of FIGS. 8A-8D.
FIG. 12D shows an exemplary spatial gap that may be achieved using the assemblies shown in FIGS. 12A-12C.
FIG. 12E is a detail of an exemplary arrangement of correlated magnets that may be provided in the assemblies shown in FIGS. 12A-12C.

FIGS. 12A and 12B show an example of correlated magnet assemblies 18, 19 that may be included in the system 14. In the example shown, an array of correlated magnets are embedded in or otherwise attached to opposite surfaces of the assemblies 18, 19. For example, a primary or central array of magnets 21 may be provided, e.g., generally centrally located on the surface of the assemblies 18, 19, that may be coded to control the alignment between the two corresponding magnet assemblies 18, 19. A plurality of secondary magnets 2 may be provided around the central array 21, e.g., spaced apart symmetrically from one another around the central array 21, to control and/or substantially maintain the spatial gap 6*a* or 6*b* via magnetic field force interaction in terms of attraction and repelling forces. FIG. 12C shows an example of this interaction, while FIG. 12D shows an exemplary predetermined spatial gap 6*a* that may be provided. FIG. 12E is a detail showing an exemplary correlated magnet configuration 22 that may be provided on the assemblies 18, 19.

Figures 13A, 13B, 13C, 13D, 13E:
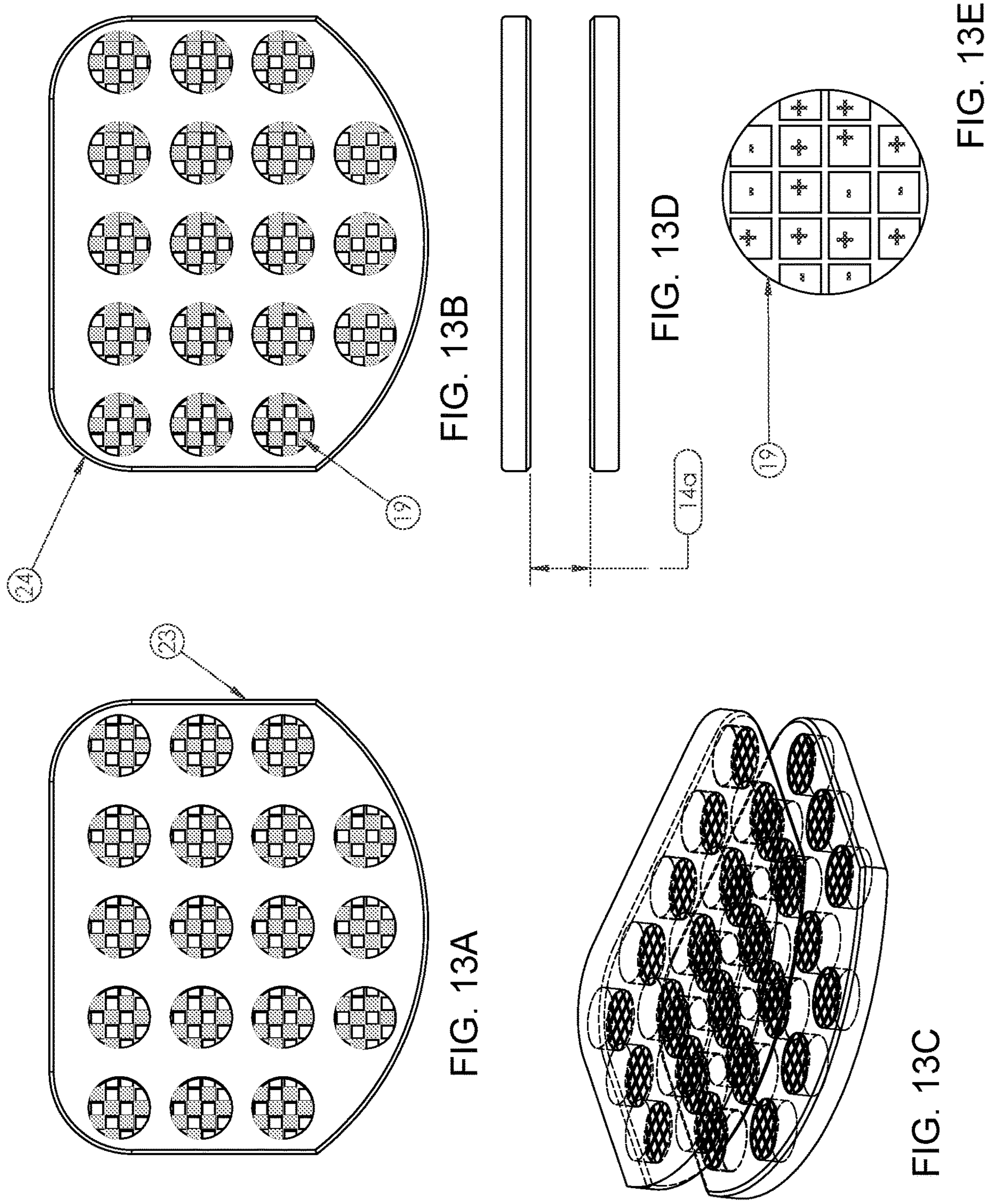
FIGS. 13A-13C show another example of correlated magnet assemblies that may be included in the system of FIGS. 8A-8D.
FIG. 13D shows an exemplary spatial gap that may be achieved using the assemblies shown in FIGS. 13A-13C.
FIG. 13E is a detail of an exemplary arrangement of correlated magnets that may be provided in the assemblies shown in FIGS. 13A-13C.

FIGS. 13A-13B show another example of correlated magnets assemblies 23, 24 programmed with different corresponding magnetic field codes to address the compression and lateral forces exerted on the two vertebral bodies. In this example, a plurality of arrays of magnets are provided on the surfaces of the assemblies 23, 24 that are spaced apart from one another in a desired arrangement. For example, the arrays may all include similar sized arrays arranged in a symmetrical pattern, with the Maxels being identical or different based on their location on the assemblies 23, 24, as desired. FIG. 13C shows an example of the interaction of the assemblies 23, 24, while FIG. 13D shows an exemplary predetermined spatial gap 6*a* that may be provided. FIG. 13E is a detail showing an exemplary correlated magnet configuration 19 that may be provided on the assemblies 23, 24.

The use of this system 14 may alleviate compression issues that may otherwise be imposed on a intervertebral disk, e.g., a damaged disk that is removed before implanting the system 14, by managing compression and/or lateral forces while allowing natural degrees of spine motion, via the programmed magnetic fields generated by the correlated magnets.

Figures 14A, 14B:
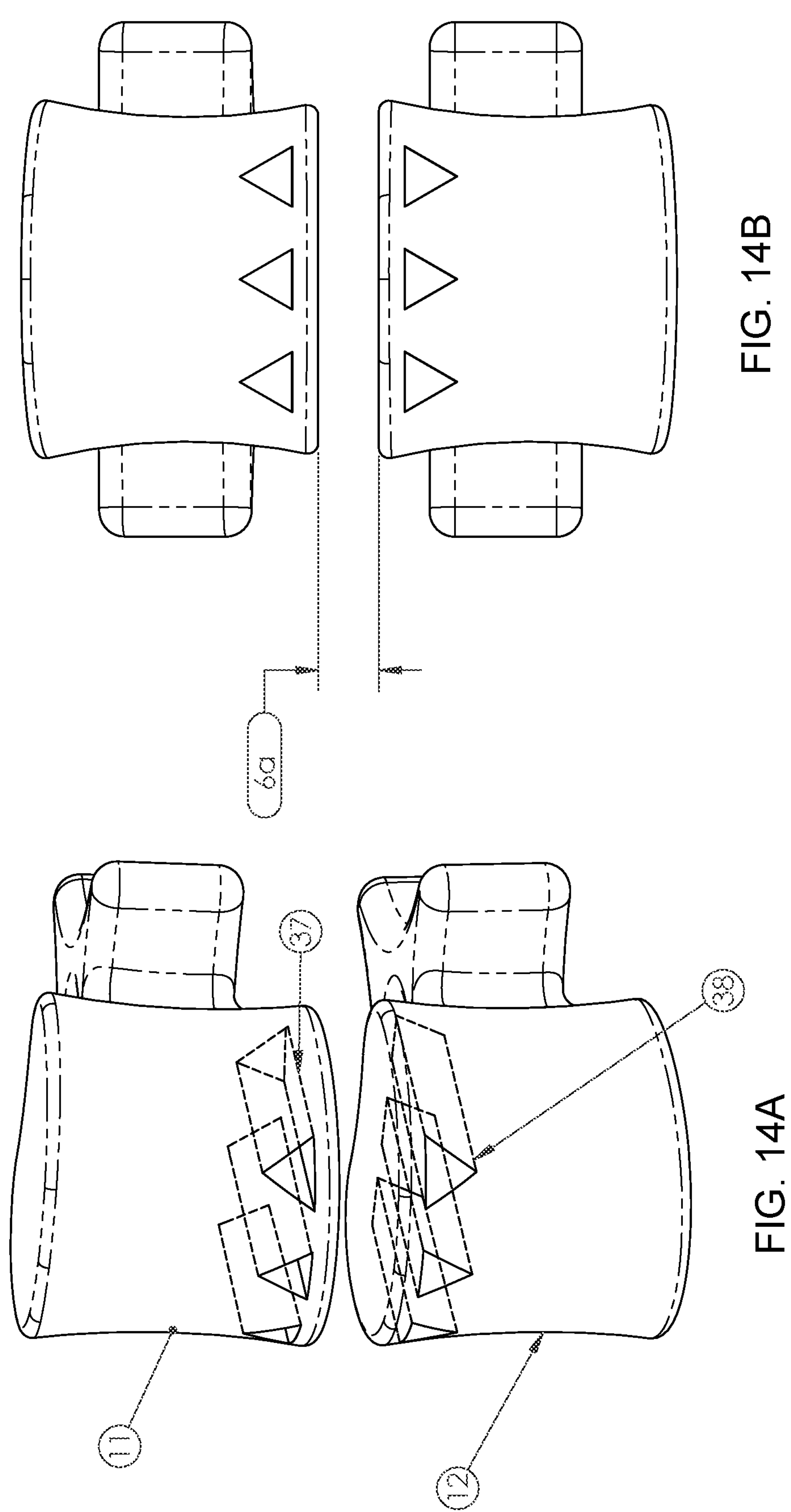
FIGS. 14A and 14B another example of a system of correlated magnet implants implanted directly into adjacent vertebral bodies to achieve a desired spatial gap.

Turning to FIGS. 14A and 14B, another example of a system including correlated magnets is shown that may be implanted into vertebral bodies 11, 12 of vertebrae of a subject's spine. In this example, first and second sets of implants 37, 38 including correlated magnets may be embedded directly into the vertebral bodies 11 and 12. For example, passages may be created directly within the bones, e.g., from the outer surface of the vertebral bodies 11, 12 to accommodate implantation of the magnets 37, 38, e.g., via normal drilling surgical techniques. Thus, if desired, the implants 37, 38 may be implanted into the vertebral bodies 11, 12 without removing the disk (not shown). Alternatively, magnet implants may be embedded into or other attached to the opposing surfaces of the vertebral bodies 11, 12. The spatial gap 6*a* may or may not include the original intervertebral disk 13 (not shown).

Optionally, disk material may be provided between the implants of a system, such as the system 14 shown in FIGS. 8A-8D. The disk material may be inserted after implantation of the system 14 or may be integrated into the system 14, e.g., to provide a single artificial disk assembly that may be implanted between vertebral bodies 11, 12, e.g., to replace a damaged native disk. For example, FIGS. 15A-15D show an artificial intervertebral disk assembly that includes artificial disk material 41 in between magnet plate assemblies 42, which have magnets 37, 38 embedded or otherwise fixed therein. Artificial disk 41, which may be permanently attached to or simply compressed between the plate assemblies 42, may have the configuration/geometry similar to the original disk (not shown) previously removed (or having a desired height greater than the original disk, e.g., if the disk was compressed or otherwise damaged). The interaction of the magnetic fields may substantially maintain an adequate spatial gap during articulation of the vertebral bodies 11, 12, e.g., as shown in FIG. 15D. In addition, the artificial disk 41 may be formed from material having a desired rigidity or flexibility, e.g., to transmit or absorb forces encountered by and/or allow desired movement between the vertebral bodies 11, 12, while the magnets 37, 37 substantially maintain the desired spatial gap and/or relative orientation of the vertebral bodies 11, 12.

Hip Joint Application

Figures 16A, 16B, 16C:
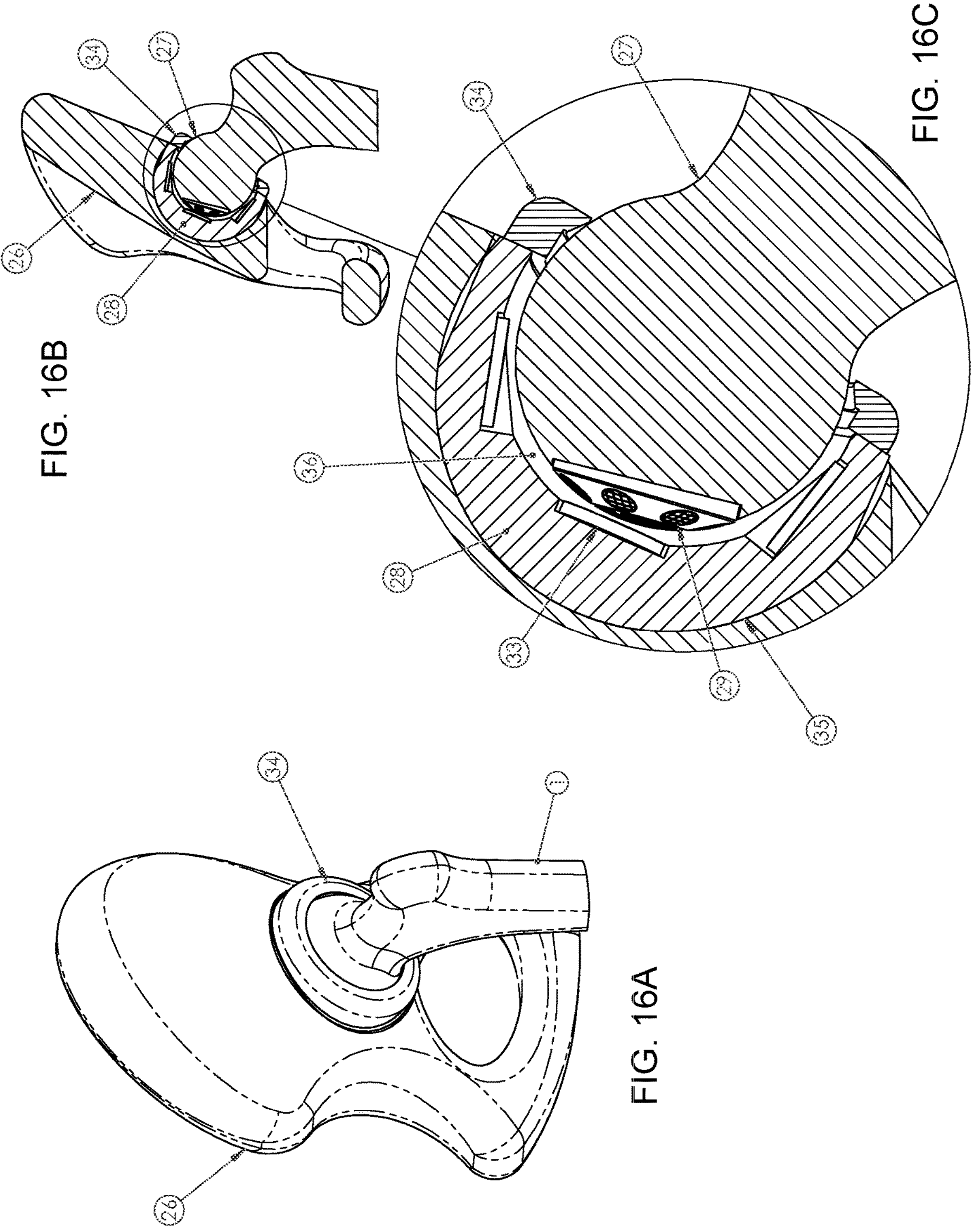
FIG. 16A shows a hip joint including an implanted system including correlated magnet assemblies implanted on a femur head and in an acetabulum of the hip joint.
FIGS. 16B and 16C are cross-sectional views of the hip joint of FIG. 16A showing components of the implanted correlated magnet assemblies.

Turning to FIGS. 16A-16C, another example of a correlated magnet system is shown that may be implanted at a subject's hip joint, i.e., including the pelvis 26 and femur 1, that may be designed to substantially manage compression forces and/or rotational motion between the head 27 of the femur 1 and the acetabulum 35 of the pelvis 26. FIGS. 16B and 16C are cross sectional side views of the hip joint, showing a spatial gap 36 between a magnet assembly 33 implanted in the acetabulum 35 and a corresponding magnet assembly 29 mounted to the head 27 of the femur 1. Optionally, a locking ring 34 or other anchor may be provided to hold the femur head 27 in place with respect to acetabulum 35.

Figures 17A, 17B, 17C:
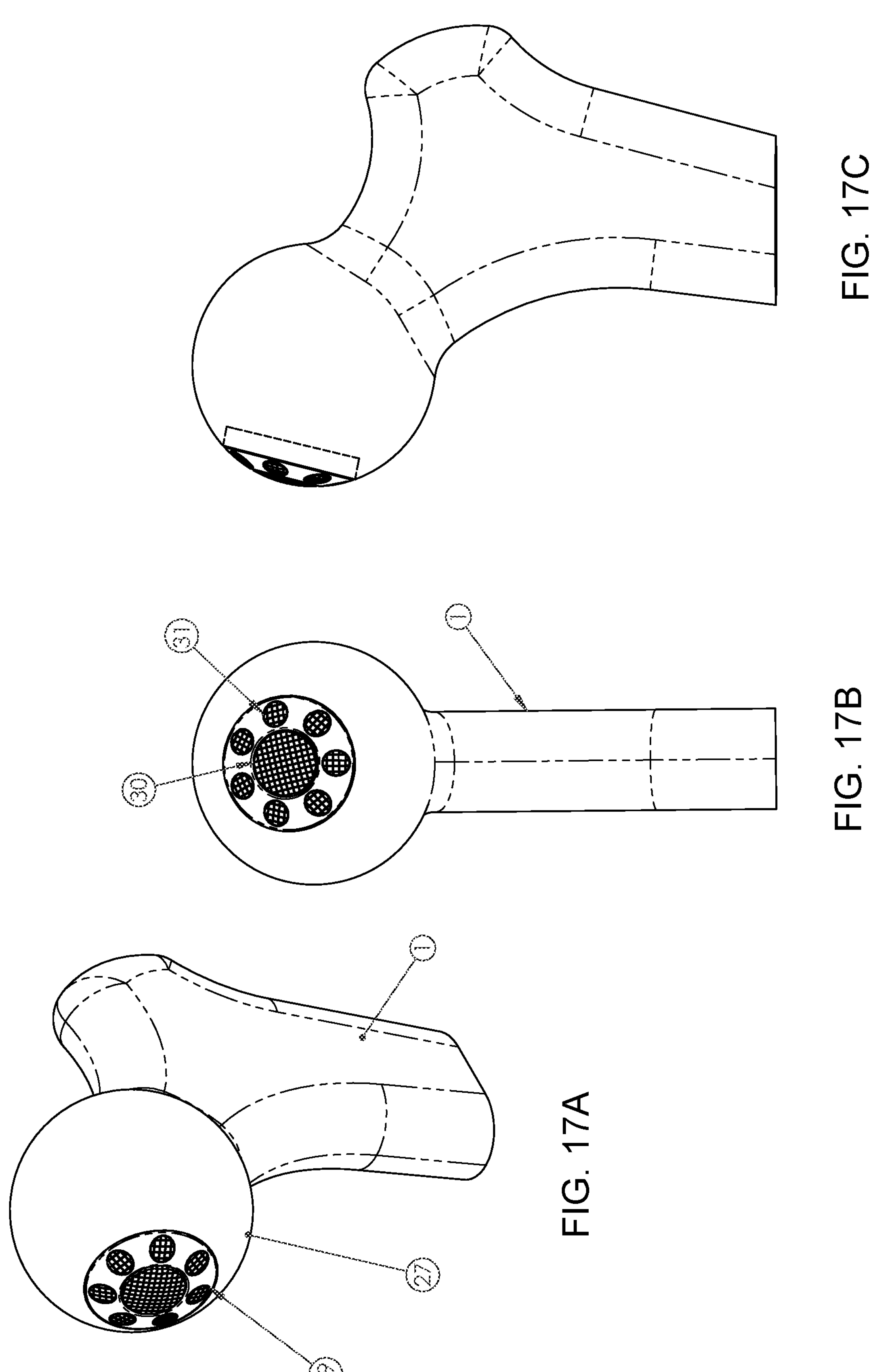
FIGS. 17A-17C are various views of an exemplary correlated magnet assembly mounted to a femur head.

With additional reference to FIGS. 17A-17C, an example of a femur head 27 is shown with an embedded correlated magnet assembly 29. FIG. 17B shows an exemplary array of magnet 30, 31 that may be provided on the assembly 33 designed to interact with the corresponding magnet assembly 33. For example, a central array of magnets 30 may be programmed to generate a magnetic field with attraction forces up to a specific spatial gap 36 with repulsion forces at a smaller spatial gap 36. A plurality of secondary arrays of magnets 31 may surround the central magnet array 30 to substantially control and/or maintain the predetermined spatial gap 36 during rotational motion of the femur 1 relative to the pelvis 26. In addition or alternatively, one or more sets of correlated magnets may be embedded/implanted at or below the articulation surface of the femur head 27 (not shown).

Figures 18A, 18B, 18C:
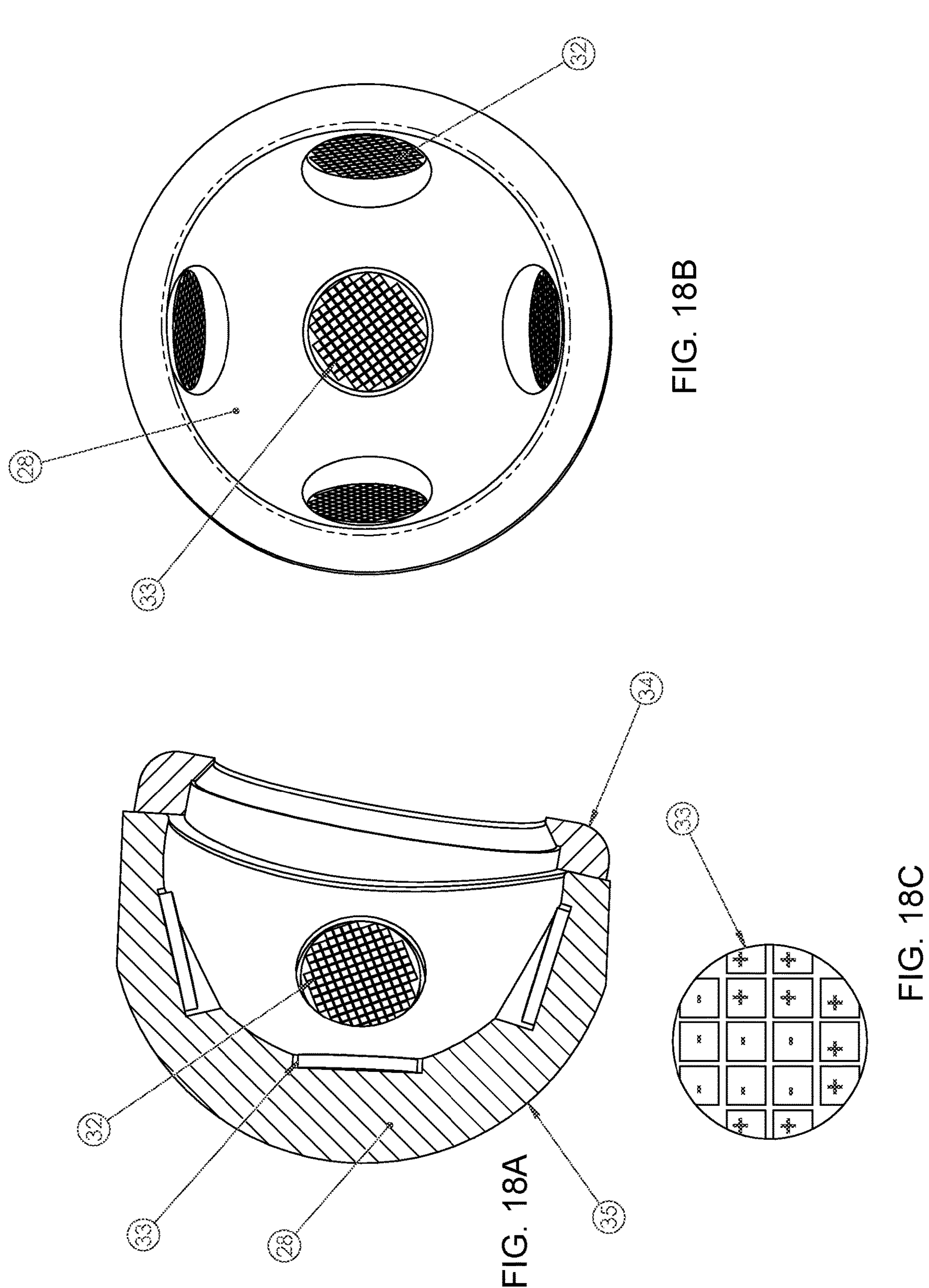
FIGS. 18A and 18B show an exemplary correlated magnet assembly configured to be implanted in the acetabulum.
FIG. 18C is a detail of a correlated magnet assembly.

FIGS. 18A-18C show an example of the acetabulum 35 with a magnet assembly 28 and locking ring 34. As shown, each individual array of magnets may be embedded or otherwise implanted in the bone surrounding the acetabulum 35. Alternatively, a plurality of arrays of magnets may be provided on an integral socket body (not shown) that may be sized to be implanted in the acetabulum 35. The magnets 33, 32 of the assembly 28 may be configured to substantially manage compression and rotational forces in order to maintain the desired spatial gap 36. The magnetic code programmed into the Maxels of the magnet surface, e.g., as shown in FIG. 18C, may be designed to generate a field interaction adequate to overcome torque and compression forces due to joint motion in a natural fashion; while preventing bone on bone contact and helping to increase blood flow to the surrounding tissue and cartilage. In addition or alternatively, one or more sets of correlated magnets may be embedded/implanted at or below the articulation surface of the acetabulum 35 (not shown).

In another alternative, a combination of magnets may be embedded directly on one bone structure and a magnet assembly 28 may be secured to the articulating surface of acetabulum 35 (not shown). In yet another alternative, magnets or magnet assemblies may be embedded or mounted onto artificial hip joint replacement components (not shown), e.g., to substantially manage the rotation and/or compression forces of the hip joint (not shown).

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system for supporting first and second adjacent vertebrae of a spine, comprising:

a first plate configured for mounting to an upper surface of a first vertebral body;

a second plate configured for mounting to a lower surface of a second vertebral body opposite the upper surface of the first vertebral body; and first and second correlated magnet assemblies configured to be secured to the first and second plates, respectively, to provide a desired spatial gap between the first and second vertebral bodies, wherein each of the first and second correlated magnet assemblies comprises a plurality of coded correlated magnets (Maxels) programmed to generate magnetic field interaction suitable to maintain the desired spatial gap when compression and lateral forces are applied by the vertebral bodies, wherein each of the first and second correlated magnet assemblies comprises a plurality of magnet arrays spaced apart from one another on a surface of the assemblies opposite the contact surface, and wherein the plurality of magnet arrays on each of the first and second correlated magnet assemblies comprise a central array programmed to maintain alignment of the vertebral bodies and a plurality of secondary arrays spaced apart around the central array programmed to maintain a desired spatial gap between the first and second vertebral bodies during movement of the spine.

2. The system of claim 1, wherein each plate includes a contact surface configured for placement against the respective vertebral body and one or more features extending from the contact surface for securing the plate to the respective vertebral body.

3. The system of claim 2, wherein the one or more features comprise a pair of ridges extending from the contact surface configured to be received in respective grooves formed in the respective vertebral body.

4. The system of claim 3, wherein the ridges extend substantially parallel to one another.

5. The system of claim 2, wherein each plate further comprises a socket opposite the contact surface for receiving a respective correlated magnet assembly.

6. The system of claim 5, wherein each plate includes a sidewall extending partially around a perimeter of the plate to define the socket such that the respective magnet assembly may be slid into the socket from one edge of the plate.

7. The system of claim 6, wherein the sidewall includes one or more features to prevent the magnet assembly received in the socket from separating from the plate.

8. The system of claim 7, wherein the one or more features comprise a rim extending at least partially around a perimeter of the sidewall.

9. The system of claim 1, wherein the secondary arrays are smaller than the central array.

10. The system of claim 1, wherein each of the magnet arrays comprises a plurality of coded correlated magnets (Maxels).

11. The system of claim 1, wherein the secondary arrays are spaced apart symmetrically from one another around the central array.

12. The system of claim 1, wherein the central array and the secondary arrays have the same arrangement on each of the first and second correlated magnet assemblies.

13. A method for supporting a first and second vertebrae of a spine, comprising:

mounting a first plate to an upper surface of a first vertebral body;

mounting a second plate to a lower surface of a second vertebral body opposite the upper surface of the first vertebral body;

securing a first correlated magnet assembly to the first plate; and securing a second correlated magnet assembly to the second plate such that the magnet assemblies are spaced apart from one another to provide a desired spatial gap between the first and second vertebral bodies, wherein each of the first and second correlated magnet assemblies comprises a plurality of coded correlated magnets (Maxels) programmed to generate magnetic field interaction suitable to maintain the desired spatial gap when compression and lateral forces are applied by the vertebral bodies, wherein each of the first and second correlated magnet assemblies comprises a plurality of magnet arrays spaced apart from one another on a surface of the assemblies opposite the contact surface, and wherein the plurality of magnet arrays on each of the first and second correlated magnet assemblies comprise a central array programmed to maintain alignment of the vertebral bodies and a plurality of secondary arrays spaced apart around the central array programmed to maintain a desired spatial gap between the first and second vertebral bodies during movement of the spine.

14. The method of claim 13, wherein mounting the first plate comprises:

forming an elongate groove in the upper surface; and inserting an elongate ridge extending from a contact surface of the first plate into the elongate groove.

15. The method of claim 13, wherein mounting the first plate comprises:

forming a pair of elongate grooves in the upper surface; and inserting a pair of elongate ridges extending from a contact surface of the first plate into the elongate grooves.

16. The method of claim 15, wherein the pair of elongate grooves extend from an outer edge of a cortical rim of the first vertebral body at least partially across towards an opposite edge.

17. The method of claim 16, wherein the first plate is slid across the upper surface while the ridges slide into the elongate grooves.

18. The method of claim 13, wherein the secondary arrays are smaller than the central array.

19. The method of claim 13, wherein the secondary arrays are spaced apart symmetrically from one another around the central array.

20. The method of claim 13, wherein the central array and the secondary arrays have the same arrangement on each of the first and second correlated magnet assemblies.

* * * * *